United States Patent [19]

Oono et al.

[11] Patent Number: 4,739,480

[45] Date of Patent: Apr. 19, 1988

[54] RADIATION IMAGE REPRODUCING APPARATUS WITH IMAGE STORAGE ID CODE FOR IDENTIFYING EXPOSURE DATA FILE

[75] Inventors: Hiroshi Oono; Tsutomu Teshima, both of Ashigara, Japan

[73] Assignee: Fuji Photo Film Co., Ltd., Kanagawa, Japan

[21] Appl. No.: 936,923

[22] Filed: Nov. 28, 1986

Related U.S. Application Data

[63] Continuation of Ser. No. 786,355, Oct. 11, 1985, abandoned, which is a continuation of Ser. No. 435,270, Oct. 19, 1982, abandoned.

[30] Foreign Application Priority Data

Oct. 26, 1981 [JP] Japan ................................ 56-171182
Oct. 26, 1981 [JP] Japan ................................ 56-171183
Oct. 26, 1981 [JP] Japan ................................ 56-171184

[51] Int. Cl.$^4$ .......................... A61B 6/00; G06K 1/12; H05G 1/26
[52] U.S. Cl. ................................... 364/414; 378/165; 378/166
[58] Field of Search ................... 364/414; 378/98, 99, 378/165, 166; 235/494; 250/271, 327.2; 354/105, 109

[56] References Cited

U.S. PATENT DOCUMENTS

| 3,590,244 | 6/1971 | Kullman | 378/165 |
| 3,942,016 | 3/1976 | Schatz | 378/165 X |
| 4,217,046 | 8/1980 | Weinstein et al. | 354/76 |
| 4,250,389 | 2/1981 | Brendl et al. | 378/166 |
| 4,283,621 | 8/1981 | Pembroke | 235/375 |
| 4,284,889 | 8/1981 | Kato et al. | 250/327.2 |
| 4,320,296 | 3/1982 | Ishida et al. | 250/327.2 |
| 4,383,329 | 5/1983 | Kröbel et al. | 378/166 |
| 4,420,234 | 12/1983 | Dolejsi et al. | 353/122 |
| 4,433,429 | 2/1984 | Finkenzeller et al. | 378/165 X |
| 4,441,807 | 4/1984 | Bartz | 355/40 |
| 4,507,797 | 3/1985 | Kato | 378/165 |
| 4,611,247 | 9/1986 | Ishida et al. | 364/414 X |
| 4,641,242 | 2/1987 | Kimura | 364/414 |

FOREIGN PATENT DOCUMENTS

| 0014436 | 8/1980 | European Pat. Off. | 378/166 |
| 0799727 | 1/1981 | U.S.S.R. | 378/165 |

OTHER PUBLICATIONS

Kaufman, L. et al., "A Large Capacity Image Acquisition, Processing and Display System for Nuclear Medicine", Conference: Application of Optical Instrumentation in Medicine, Nov. 1973, 35–42.

PALM 3 User's Guide, Oct. 1982, 1–17.

Pistor, P. et al., "Digital Image Processing in Nuclear Medicine, Part 2", *Kerntechnik,* vol. 14, No. 8, Aug. 1972, 353–9.

*Primary Examiner*—Jerry Smith
*Assistant Examiner*—Clark A. Jablon
*Attorney, Agent, or Firm*—Sughrue, Mion, Zinn, Macpeak and Seas

[57] ABSTRACT

A data processing system for a radiation image reproducing apparatus includes an input device for entering an identification code assigned to a radiation image storage panel and data related with an exposure at an exposing device when the storage panel is exposed to an imagewise radiation. The input device is associated with the exposing device.

27 Claims, 8 Drawing Sheets

| TERMINAL UNIT CODE | OBJECT DATA | EXPOSURE DATA | IMAGING DATA |
|---|---|---|---|

FIG. 9B

| TERMINAL UNIT CODE | PANEL ID CODE |
|---|---|

RADIATION IMAGE REPRODUCING APPARATUS WITH IMAGE STORAGE ID CODE FOR IDENTIFYING EXPOSURE DATA FILE

This is a continuation of application Ser. No. 786,355, filed Oct. 11, 1985, now abandoned, which is a continuation of application Ser. No. 435,270, filed Oct. 19, 1982, abandoned.

BACKGROUND OF THE INVENTION

1. Field of the Invention

The present invention relates to a data processing system for radiation image reproducing apparatus and, more particularly, to a data processing system for a radiation image reproducing apparatus which includes at least one exposing device for exposing a stimulable phosphor sheet to radiation transmitted through an object in order to store a latent image of the object in the sheet, a reading device for photoelectrically reading, afterwards, the latent image stored in the sheet by exposing the sheet to stimulating rays, and an image reproducing device for reproducing the image based on an electric signal which is read by the reading device.

2. Description of the Prior Art

Image reproducing apparatus of the type described have been proposed as disclosed in U.S. Pat. No. 3,859,527. From the viewpoint of cost performance of the entire system, it is preferable that numerous stimulable phosphor sheets exposed by a number of remote exposing devices be managed concentratively in a single radiation image reproducing room or, as it will be referred to herein, an image processing room. The conventional identification data system, however, has not presented a solution to the problem of how to match the individual stimulable phosphor sheets with the information concerned with patients or like objects and exposures. To accomplish a high diagnostic performance, such an image reproducing system also requires that information on exposure conditions and information on image storage conditions in stimulable phosphor sheets, e.g. distributions of stored radiation amounts, be entered into an image processing computer of the system properly matched with the individual sheets.

Due to the low optical sensitivity of stimulable phosphor sheets, it is difficult to record identification data on such sheeets by an optical process heretofore employed by, for example, the radiation photographing system which utilzes silver salt photography. In light of this, if one intends to employ an image reproducing processing system as disclosed in U.S. Pat. No. 3,859,527 which uses sheets of stimulable phosphor in order to establish a centralized management of image reproducing processes, one could propose a system in which a serial number is assigned to each stimulable phosphor sheet and recorded on a slip together with object data particular to a patient, such as the name, date of birth and sex, and exposure data, such as the date and conditions of exposure and the exposed portion. Such slips are conveyed to an image processing room. In this room, when the image stored in each sheet is to be reproduced, the various data are manually entered into an image processing computer based on the slip associated with the sheet. This kind of system, however, consumes a significant amount of manual work and involves a great possibility of errors in manipulation because it has to concentratively manage numerous sheets which are often presented in various configurations.

SUMMARY OF THE INVENTION

It is therefore an object of the present invention to provide, for a radiation image reproducing apparatus, a data processing system which eliminates the drawback discussed above and facilitates concentrative management of numerous kinds of a number of radiation image storage panels or sheets while requiring a relatively simple manual operation and, therefore, minimizing the liability of errors.

In order to achieve this object, a data processing system embodying the present invention includes input means for entering an identification code assigned to a radiation image storage panel and data related with an exposure at an exposing device when the panel is exposed to an image radiation, the input means being associated with the exposing device.

In an aspect of the present invention, the data processing system may include transmission means for transmitting to an image reproducing device entered data related with an exposure by matching the data with an identification code assigned to a radiation image storage panel.

In another aspect of the present invention, the identification code may be recorded by recording means in response to an exposure at an exposing device.

In still another aspect of the present invention, the data processing system may include storage means for storing the entered data related with the exposure in association with the identification code assigned to the panel, reading means for reading the identification code on the sheet after an exposure, and searching means for searching for data matching with the identification code read by the reading means out of the storage means.

In the present invention, the stimulable phosphor may be defined as a phosphor which, after exposure to an initial radiation like X-rays, $\alpha$-rays, $\beta$-rays, $\gamma$-rays and ultraviolet rays, emits light of the amount associated with the energy of the stored radiation when stimulated optically.

Preferably, a stimulable phosphor applicable to the present invention emits light having a wavelength within the range of 300 to 500 nm in response to stimulating rays having a wavelength within the range of 600 to 700 nm, as disclosed in U.S. Pat. No. 4,258,264. One example of this phosphor is rare earth activated alkaline earth metal fluorohalide phosphor, as shown in Japanese Patent Laid-Open Publication No. 12143/1980, a phosphor represented by the formula $(Ba_{1-x-y}, Mg_x, Ca_y)FX:aEu^{2+}$ wherein X is at least one of Cl and Br, x and y are numbers satisfying $0 < x+y \leq 0.6$ and $xy \neq 0$, and a is a number satisfying $10^{-6} \leq a \leq 5 \times 10^{-2}$. Another example of this phosphor is, as described in U.S. Pat. No. 4,239,968, a phosphor represented by the formula $(Ba_{1-x}, M^{II}_x)FX:yA$ wherein $M^{II}$ is at least one of Mg, Ca, Sr, Zn and Cd, X is at least one of Cl, Br, and I, A is at least one of Eu, Tb, Ce, Tm, Dy, Pr, Ho, Nd, Yb and Er, x is a number satisfying $0 \leq x \leq 0.6$, and y is a number satisfying $0 \leq y \leq 0.2$. Further, as the stimulable phosphor to be used in the present invention can be used ZnS:Cu, Pb; $BaO.xAl_2O_3$:Eu wherein $0.8 \leq x \leq 10$; and $M^{II}O.xSiO_2$:A wherein $M^{II}$ is Mg, Ca, Sr, Zn, Cd or Ba, A is Ce, Tb, Eu, Tm, Pb, Tl, Bi or Mn, and x is a number satisfying $0.5 \leq x \leq 2.5$, as disclosed in U.S. Pat. No. 4,236,078. Furthermore, another material which can be used as the stimulable phosphor is LnOX:xA wherein Ln is at least one of La, Y, Gd, and Lu, X is at least one of Cl and Br, A is at least one of Ce and Tb, x is a number satisfying $0 \leq x \leq 0.1$, as described in U.S. Pat. No. 4,236,078. Among the above numerated phosphors, the rare earth activated alkaline earth metal fluorohalide phosphor is the most preferable, among which barium fluorohalides are the most preferable in view of the high intensity of emission of light.

For higher intensity of emission of light, use may be made of barium fluorohalides with the addition of metal fluorides as described in Japanese Patent Laid-Open Publication Nos. 2385/1981 and 2386/1981, or those with the addition of at least one of metal chlorides, metal bromides and metal iodides, as disclosed in U.S. patent application Ser. No. 367,665, now abandoned.

Further, it is desirable to color the phosphor layer of the stimulable phosphor plate including the above phosphor by use of pigments or dyes to improve the sharpness of the image obtained thereby, as disclosed in U.S. patent application Ser. No. 156,520, now U.S. Pat. No. 4,394,581.

BRIEF DESCRIPTION OF THE DRAWINGS

The objects and features of this invention will become more apparent from a consideration of the following detailed description and the drawings in which.

DESCRIPTION OF THE PREFERRED EMBODIMENTS

Figure 1:
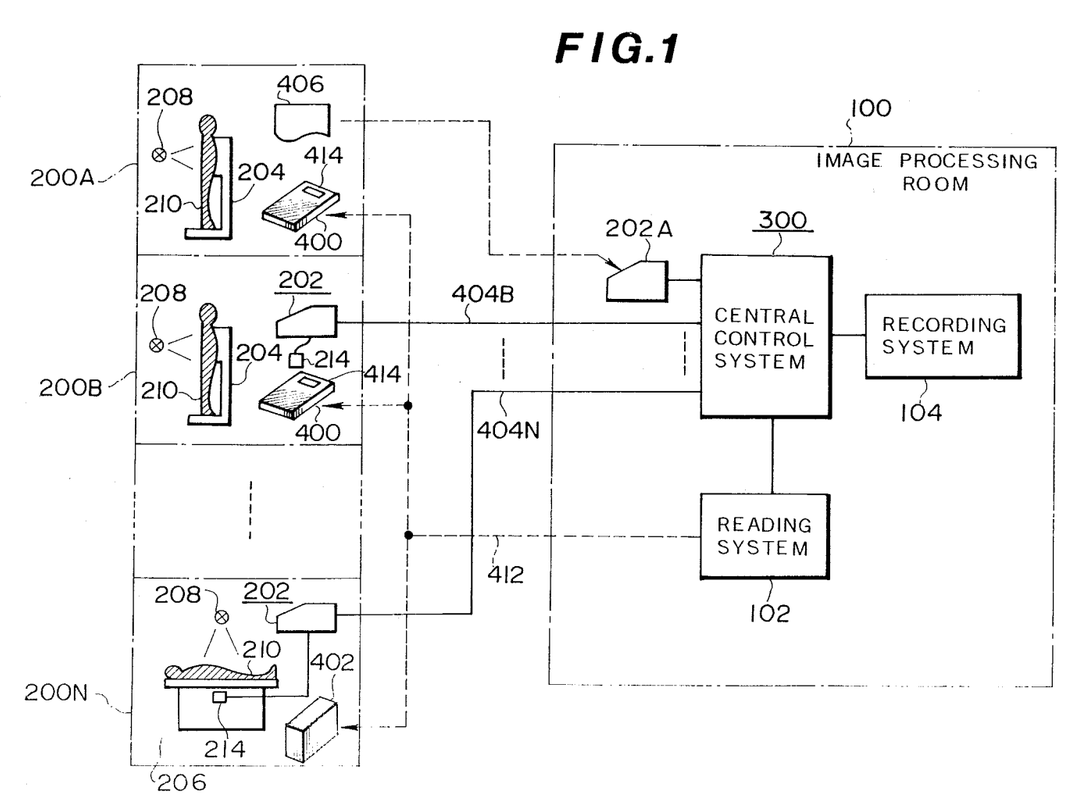
FIG. 1 is a schematic block diagram of a data processing system of the present invention which is aplied to a radiation image reproducing apparatus.

Referring to FIG. 1 of the drawings, a data processing system of the present invention generally comprises a central control system 300 located in an image processing room or station 100 and terminal units 202 located mainly in exposure rooms or sites 200B-200N. The exposure room 200B, as well as an exposure room 200A, is provided with a cassette type pedestal 204 on which a cassette 400, which, for example, encases a single radiation image storage panel or sheet, is removably loaded. The room 200N, on the other hand, is equipped with a cassette-less pedestal 206 on which a magazine 402 carrying a plurality of radiation image storage panels or sheets is removably mounted. It should be remembered, however, that such an arrangement of exposure rooms is only for illustrative purpose, and other similar rooms as indicated by phantom lines in the figure may also be included. The radiation room 200A, though not limited thereto, lacks the terminal unit 202 installed in each of the other rooms. The rooms 200A-200N may be physically located at long or short distances from each other and, of course, from the image processing room 100.

The central control system 300 is connected to the terminal units 202 in the rooms 200B-200N by communication circuits 404B-404N, respectively. In the image processing room 100, the central control system 300 is connected with a reading system 102 for reading an image stored in an exposed radiation image storage panel and an image recording system 104 for reproducing a visible image from processed image signals. The central control system 300 controls the operations of the whole system such as processing image signals read by the reading unit 102 into a form suitable for recording at the recording unit 104 and processing data received from the individual terminal units 202. Directly associated with the central control system 300 in the room 100 is a terminal unit 202A through which data can be inputted based on a memo 406 or the like prepared in, for example, the room 200A, which lacks the terminal unit 202.

Figure 2:
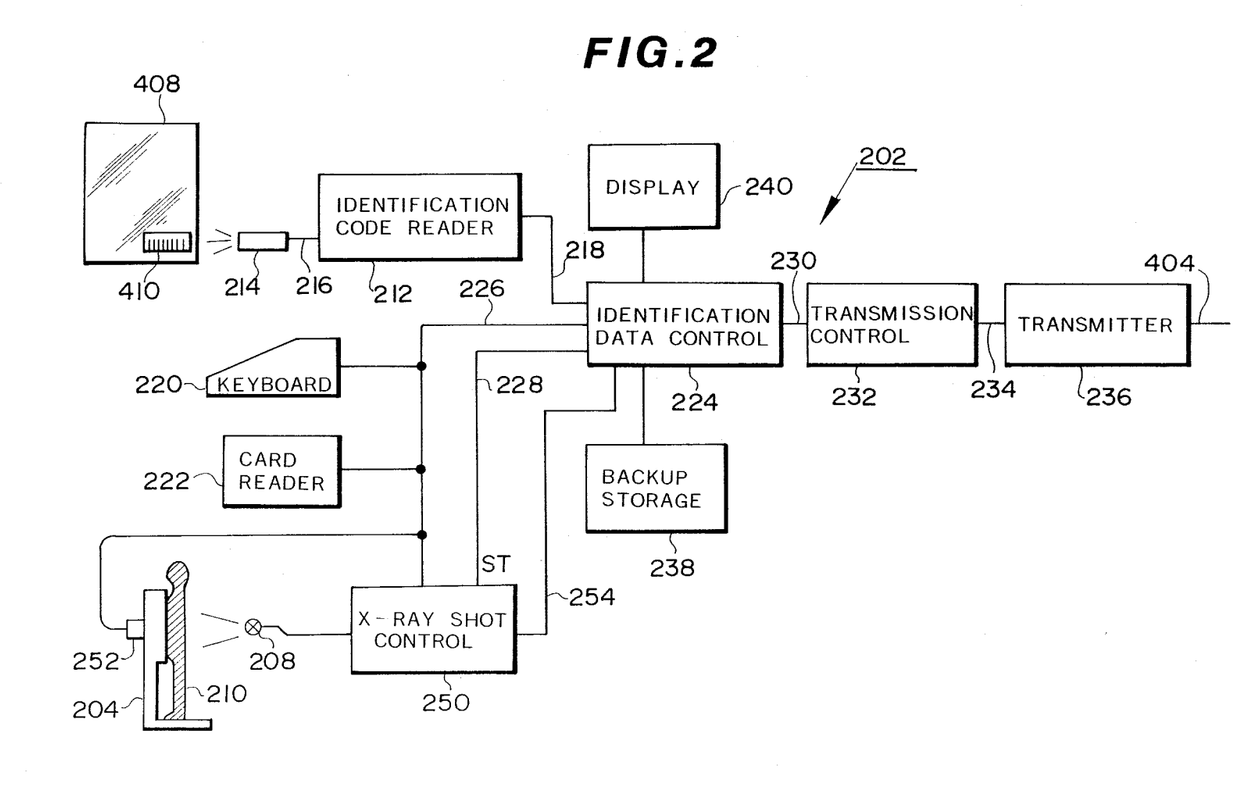
FIG. 2 is a block diagram indicating in detail an arrangement of a terminal unit shown in FIG. 1.

In accordance with the present invention, as shown in FIG. 2, a label 410 is adhered to a predetermined position on each radiation image storage panel 408 which is stored in a cassette 400 or a magazine 402. The label 410 carries an identification code assigned to the specific sheet 408, e.g. a serial number. The identification code is of the type which can be automatically read by mechanical, optical, magnetic or electrostatic means. From the viewpoint of concentrative management and processing of numerous such panels 408, it is advantageous that the code include human readable numerals and/or characters. While the illustrated embodiment employs bar codes to be optically read and numerals to be read by an operator, they may be replaced by any other type of codes such as characters and/or numerals which can be read by an optical character reader (OCR), perforations or magnetically recorded codes.

Numerous panels 408, each provided with its own identification code, are encased in cassettes 400 and magazines 402 and distributed from the image processing room 100 to the individual exposure rooms 200A-200N. In each of the rooms 200A-200N, an object, a human body 210 in this embodiment, is exposed to X-rays emitted from an X-ray source 208. The X-rays transmitted through the human body 210 impinge on a panel 408.

The X-ray transmission image of the human body 210 is stored in the panel 408. All the exposed panels 408 are fed from the rooms 200A-200N to the reading system 102 in the image processing room 100 so as to be read thereby concentratively. The panels 408, after having undergone image reading, are distributed back to the rooms 200A-200N to be used for other exposures. The path travelled by the panels 408, are indicated by the broken line paths 412 in FIG. 1.

After the human body 210 in each room 200B-200N is exposed to radiation, the terminal unit 202 is operated to enter the identifiction code assigned to the panel 408 as well as various data related with the human body 210 and the exposure. Such code and data are transferred to and stored in the central control system 300. As to the room 200A which lacks the terminal unit 202, the code and data are recorded on, for example, a slip 406 and such slips 406 are brought afterwards to the image processing room 100 to be inputted through the terminal unit 202A. The data related with the respective panels 408 exposed in the rooms 200A-200N are stored in the central control system 300. Then, the reading system 102 reads the identification codes of the panels 408 fed thereto from the rooms 200A-200N and supplies them to the central control unit 300. The central control unit 300, based on the identification codes, searches for matching data stored therein and then, based on the searched data, determines image reading conditions and image signal processing conditions to process image signals. The image recording system 104 records on a recording medium not only the reproduced image but the data concerned with the object and other necessary data as part of the visible image.

The data consists of object data particular to the object or human body 210 and exposure data which will be required afterwards to determine image processing conditions at the central control system 300.

The object data may include the name data of birth, sex, chart number (code) and others particular to a patient. The object data may be entered into the system by checking the patient's identification card (consulation ticket) or chart. The exposure data, on the other hand, may include management data such as the date and time of exposure and the code of an exposure room or location, statistical data such as the number of films used, various exposure conditions such as X-ray tube voltage/current, X-ray radiation time and distance between the X-ray tube and the film (FED), the image processing conditions such as frequency and tone processings of the image, the exposed object's part as typified by the chest or abdomen, and the exposing method such as with or without a contrast medium. Use may be made of a keyboard, dials or switches for entering the exposure data.

The data mentioned above may additionally include imaging data such as a distribution of stored radiation amounts in the panel 408. The imaging data is obtainable, for example, by locating a sensor responsive to an X-ray radiation amount (not shown) to the back of the panel 408, as disclosed in U.S. patent application Ser. No. 168,803, now U.S. Pat. No. 4,320,296. Alternatively, the distribution of stored radiation amounts and other imaging data may be provided by reading them out before reading out and reproducing a stored image, as described in Japanese Patent Application Nos. 165111/1981, 165112/1981 and 165113/1981.

Referring to FIG. 2, the terminal unit 202 installed in each of the rooms 200B-200N includes an identification code reading unit 212 adapted to read an identification code assigned to a panel 408 and carried on the label 410 adhered to the panel 408. The identification code reader 212 is supplied through a lead 216 from a sensor 214 which senses the identification code optically, for example. The optical sensor 214 has a light emitting element (not shown) for emitting a light beam onto the label 410 and a photoelectric transducer (not shown) for converting light reflected from the label 410 into an electric signal. In the case of the exposure room 200B with the cassette type pedestal 204, the sensor 214 may take the form of a pen type scanner which is manually moved to scan the identification code on the label 410 through an opening 414 formed in part of the cassette 400. In the case of the cassette-less pedestal 206, the sensor 214 may be located inside the pedestal 206 to face the label 410 on the panel 408. The identification code reader 212 shapes the sensor output to decode it and then delivers it to a lead 218 as a digital signal indicative of the identification code on the label 410. If desired, the reader 212 may be furnished with a function of checking an error in the identification code read out from the label 410.

The terminal unit 202 shown in FIG. 2 is provided with a keyboard 220 and a card reader 222 for the purpose of entering the previously mentioned object data and exposure data. While the keyboard 220 suffices the purpose in principle if equipped with alphanumeric keys, it will be advantageous to use in combination therewith a card reader capable of directly reading the identification card or chart of the patient 210 (e.g. magnetic card reader or punched card reader) and/or a mark sheet reader. The card reader 222 may, for example, magnetically read on identification card provided with a magnetic recording strip so as to input the object data into the system. The date and time of exposure, tube voltage and other exposure data are entered into the system through the keyboard 220. Alternatively, the exposure data may be entered through manually set dials or switches mounted on a shot control device 250 which is associated with the pedestal 204. Also, the imaging data, particularly the distribution of stored radiation amounts, may be provided by a sensor 252 associated with the pedestal 204. The keyboard 220 and card reader 222 are connected to a second input 226 of an identification data control unit 224. The identification data control unit 224 serves to control the entire terminal unit 202 and may be constituted by a microcomputer. The major function of the identification data control 224 is, for each shot, matching and identification code of a panel 408 used for the shot with the data entered through the keyboard 220 and card reader 222. The control 224 therefore includes a register or a memory for temporarily storing the identification code and input data and responds to a trigger signal ST fed thereto from the pedestal 204. As the trigger signal ST, there can be utilized a shot signal from a shot button on an operating device (not shown) associated with the pedestal 204 or a feed signal of a panel 408. In response to the trigger signal ST, the control 224 releases the stored identification code and input data to an output 230.

Figure 4:
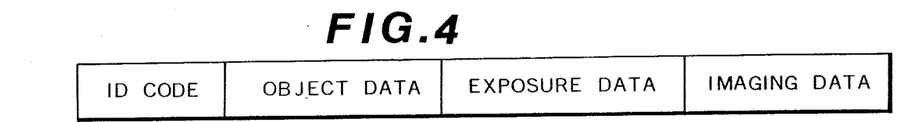
FIG. 4 is a view of an exemplary format of a message block transmitted from the terminal unit.

The output 230 of the identification data control 224 connects to a transmission control unit 232 adapted to control the transmission in conformity to a communication protocol for communication with the central control system 300 in the image processing room 100. The panel identification code and various input data such as the object and exposure data are fed through the lead 230 to the transmission control 232 to be processed thereby into a suitble length of message block or bucket. The message block or bucket is fed from the control 232 to a lead 234 in parallel with additional codes which may include a header, a trailer and like message identification codes, a control code and an error check code. The control 232 also performs the drive of a communication line 404, control of the transmission, acknowledgement of the message transmission (ACK) and recovery. An exemplary format of the message block is illustrated in FIG. 4.

The parallel output 234 of the transmission control 232 is coupled to a transmitter 236 which then transforms the parallel input into a serial signal and transmits it to the central control system 300 through the circuit 404. The circuit 404 may be constituted by an existing transmission system of the band types such as a metallic line, analog carrier line or digital line, depending on its distance to the central control system 300, type of codes and transmission rate. Where the circuit 404 is in the form of a carrier line, the transmitter 236 requires a MODEM. If the circuit 404 is of the asynchronous type, start and stop bits will also be added to the message block. Further, for quite a short distance between the terminal unit 202 and the central control system 300 as would be the case when they are located in a common building, the parallel data may be transferred from the communication control 232 directly to the central control system 300 without the intermediary of the transmitter 236.

A backup storage apparatus 238 is connected with the identification data control 224 and which may comprise a magnetic cassette tape apparatus or a floppy disc apparatus, for instance. Upon failure in the circuit 404 or the like, the identification code and various data stored in the identification data control 224 may be sequentially transferred into the magnetic cassette tape or the floppy disc and, afterwards, the tape or floppy disc may be transported to the image processing room 100. If desired, after the recovery of the circuit 404, they may be transferred together to the central control system 300 through the identification data control 224, transmission control 232 and transmitter 236.

A display unit 240 is connected with the identification data control 224 in order to provide visible indication of operating conditions of the entire terminal unit 202. Advantageously, the display 240 is constituted by a CRT display though not limited thereto and may be replaced by, a typewriter integral with the keyboard 220. The display 240 allows a person to grasp the varying conditions of the whole system and to be instructed of a procedure for entering data through the sensor 214 associated with the code reader 212, keyboard 220 or card reader 222.

To eliminate errors in operation such as a shot before data is introduced into a panel 408, an arrangement may be made such that an indication meaning "SHOOT" is not provided either visually on the display 240 or by sound unless minimum required data, e.g. identification code and patient's code, is entered. For this purpose, the identification data control 224 checks whether the minimum required data has been entered while the display 240 indicates the results of the check. Additionally, the terminal unit 202 may have an interlocking function such that the result of the check is coupled to the shot control device 250 through a lead 254 to disable the control unit 250, preventing an X-ray source 208 from being driven even if one depresses a shot button (not shown). The interlock may be of the kind which can be manually cancelled. The minimum required data for satisfying the indication "SHOOT" may be programmed in the identification data control 224.

Figure 3:
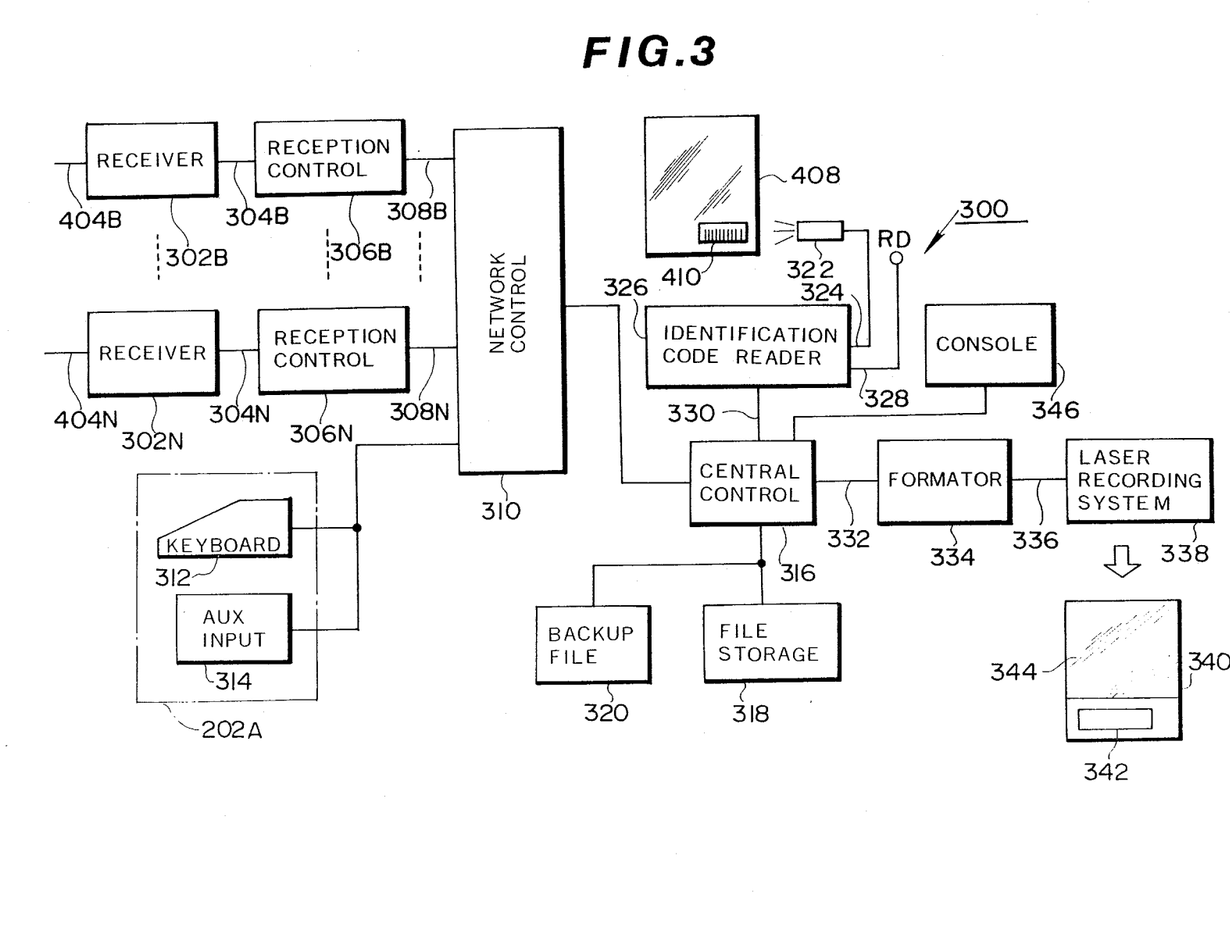
FIG. 3 is a block diagram indicating in detail an arrangement of a central control system shown in FIG. 1.

Referring to FIG. 3, the central control system 300 includes receivers 302B–302N which are respectively connected with the transmitters 236 shown in FIG. 2 by circuits 404B–404N. The receivers 302B–302N identify the bits of data signals supplied thereto through the circuits 404B–404N, shape them into digital signals and apply the digital signals to leads 304B–304N, respectively. It will be noted that when the circuits 404B–404N are carrier circuits, each receiver has to include a MODEM, particularly a demodulator.

The leads 304B–304N respectively connect to reception control units 306B–306N each of which cooperates with its associated transmission control 232 of the terminal unit 202 to perform a transmission control based on a predetermined communication protocol. The reception controls 306B–306N extract data codes out of the received message blocks or buckets and couple them in parallel form to output leads 308B–308N, respectively. The output leads 308B–308N include leads adapted for the indication of the reception of data codes. In the case where the distance between the rooms 100 and 200A–200N is very short, metallic parallel transmission may be employed omitting the receivers 302B–302N and reception controls 306B–306N.

Outputs 308B–308N of the respective reception controls 306B–306N connect to inputs of a transmission network control unit 310, which has the terminal unit 202A thereinside. As shown, the terminal unit 202A includes a keyboard 312 for entering a panel identification code and object and exposure data carried on the slip 406, which has been transported from a room lacking the terminal unit 202 such as the room 200A, and an auxiliary input device 314 for entering data from a magnetic cassette tape or from a floppy disc prepared by the backup storage 238 of the terminal unit 202. The auxiliary input apparatus 314 therefore comprises a magnetic cassette tape device and/or a floppy disc device.

The network control 310, under the control of a central control unit 316, stores the data supplied from the reception controls 306B–306B and terminal unit 202A into a file storage unit 318 in regular order. For this purpose, the network control 310 controls various channels and manages the loaded and unloaded conditions of the file. While the blocks 310 and 316 are illustrated in FIG. 3 as functionally independent blocks, they may be realized together by a microprocessor in the physical aspect. Apart from the function mentioned, the central control 316 performs various controls alloted to the central control system 300, as will be described later.

The file storage 318 is adapted to store an identification code of a panel 408 and object and exposure data corresponding to the panel 408. Preferably, the file storage 318 is comprised of a semiconductor memory. Because a semiconductor memory is volatile, a backup file 320 is employed in combination with the file storage 318 to prepare for a possible system down of the central control system 300 which would break up the data stored in the file storage 318. The backup file 320 may be constituted by a non-volatile large-capacity storage device such as a floppy disc device or a magnetic bubble memory, which is provided with redundancy to always copy the data stored in the file storage 318.

The panel 408 brought to the image processing room 100 is loaded on the reading system 102 for reading out the image stored therein. A sensor 322 is located in a sheet transfer path (not shown) of the reading system 102 so as to read the identification code assigned to the panel 408. Whatever the size of the panel 408 may be, the label 410 is positioned within a predetermined range on the panel 408 which permits the sensor 322 to read the identification code. The sensor 322 has a light emitting element (not shown) for emitting a light beam onto the label 410 on the panel 408 and a photoelectric transducer (not shown) for detecting light reflected from the label 410. An electric signal corresponding to the identification code on the label 410 appears on a lead 324 which connects to an identification code reading unit 326. This unit 326 shapes the input signal from the sensor 322 and stores it in its register (not shown) as an identification code. Such an operation of the reading unit 326 occurs in response to, for example, a control signal RD coupled thereto through a lead 328 from a microswitch which responds to the feed of the panel 408 to an image reading section (not shown) of the reading system 102. The sensor 322 and reader 326 must process numerous kinds of multiple panels 408 all at a time, and, accordingly, a reliability higher than that of the reading unit 212 at each terminal unit 202 is required. Thus, the sensor 322 and reader 326 may be equipped with a retry function and a read-out position changing function.

The identification code of the sheet 408 is delivered from the reader 326 to the central control 316 through a lead 330. Then, the central control 316 searches for the object and exposure data matching with the identification code out of the file in the file storage 318. The extracted data is fed through a lead 332 to a formator.

The formator 334 rearranges the object and exposure data into a format suitable for recording and couples it to a laser recording system 338 through a lead 336. The laser recording system 338 modulates the intensity of a laser beam in accordance with the predetermined format of object and exposure data on the lead 336, thereby providing visible reproduction of the data in a predetermined region 342 of a film 340. In this way, the film 340 forms a hard copy in which the image signal read out from the panel 408 by the reading system 102 of the terminal unit 202 and processed by the central control 316 is visibly recorded in a region 344, with the patient's name, exposure conditions and other data recorded in the region 342 as above described. A console 346 is connected with the central control 316 and provided with a display section and a control section which serve as a man-machine interface of the central control system 300. The console 346 not only facilitates monitoring the operation of the entire system as well as manipulation, but permits the identification code of the panel 408 to be entered therethrough for the manual search for the object and exposure data corresponding to the identification code. For example, when the panel 408 is determined to be erroneous by the automatic code reading at the identification code reader 326, it is loaded in the cassette 400. Then, one can read the identification code through the opening 414 of the cassette 400 and enter the identification code through a keyboard on the console 346. The subsequent search and recording of the object and exposure data occur in the same manner as in the usual automatic operation in accordance with the identification code of the panel 408.

The operation of the system described above may be summarized as follows. In the event the operator in each of the rooms 200B-200N exposes a radiation image storage panel 408 to the radiation image of an object 210, he or she causes the sensor 214 to read an identification code carried on the label 410 of the panel 408. Also, the operator inputs the object and exposure data into the system through the keyboard 220 and card reader 222. The identification code and various data are combined together for each shot by the identification data control 224. The combined information is transferred to the central control system 300 through the transmission control 232 and transmitter 236. Exposed panels 408 in each room are gathered up and brought to the image processing room 100. The central control system 300, under the control of the central control 316, sequentially stores in the file storage 318 the identification codes and object and exposure data transmitted thereto through the communication circuits 404B-404N. Before the reading system 102 reads the stored image in an exposed panel 408, the central control 316 extracts the object and exposure data matching with the identification code assigned to the panel 408 out of the file storage 318. The identification code is carried on the label 410 of the panel 408 and read out by the sensor 322 as previously discussed. The central control 316 processes the image stored in the panel 408 based on the extracted matching data and reproduces the image and data visibly on a film 340 through the formater 334 and laser recording system 338. Data from the exposure room 200A without the terminal unit 202, which may be carried on a memo 406 for example, is filed in the file storage 318 through the terminal unit 202A installed in the central control system 300.

Figure 5:
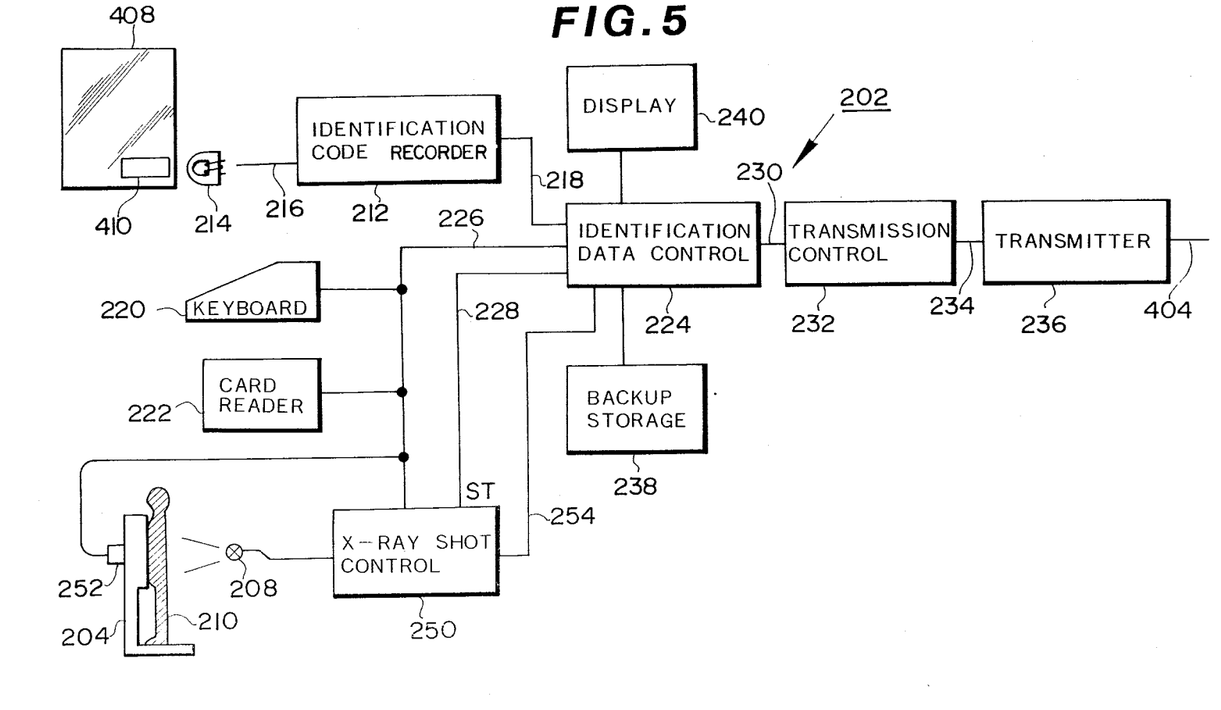
FIGS. 5 and 6 are block diagrams showing another embodiment of the present invention.
Figure 6:
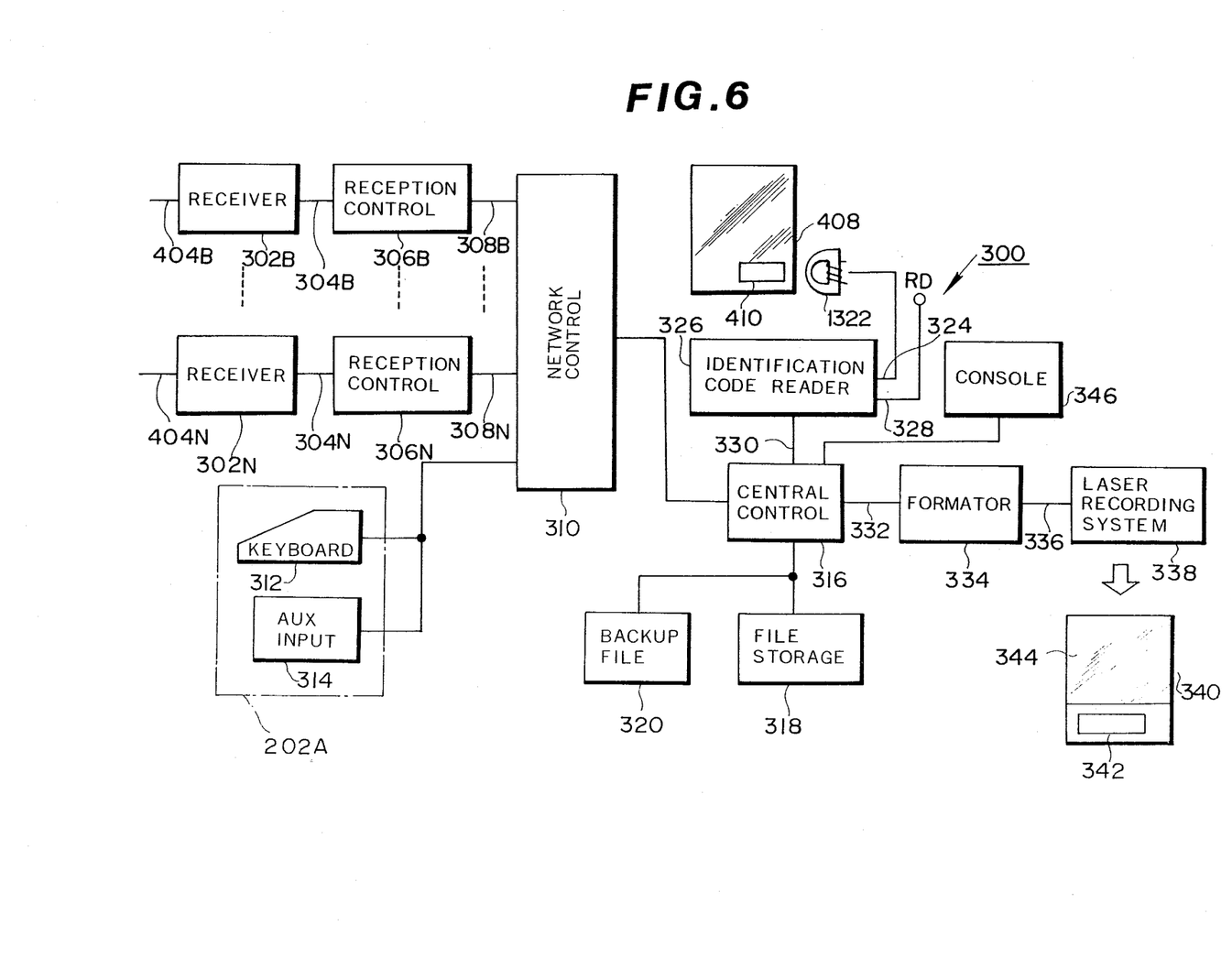

Referring to FIGS. 5 and 6, another embodiment of the present invention is illustrated in which the structural elements similar to those shown in FIGS. 2 and 3 are designated by the same reference numerals. A characteristic feature of this embodiment is that a magnetic recording medium in the form of a label 410 is adhered to a predetermined position on a radiation image storage panel 408, which is encased in a cassette 400 or a magazine 402. When the panel 408 is to be exposed to an image radiation in any one of the rooms 200B-200N, the label 410 on the panel 408 is recorded by a magnetic recording head 1214 with an identification code particular to the panel 408 and generated by the terminal unit 202.

The terminal unit 202 is provided with the magnetic recording head 1214 for recording an identification code on the label 410 carried on each panel 408, and an identification code recording unit 1212 connected with the head 1214 by a lead 216 to serve as a head drive circuit. The head 1214, in the case of the cassette type pedestal 204, is located in a position where the cassette 400 is to be inserted and, in the case of the cassette-less pedestal 206, located in a panel transfer path from the magazine 402 to face the labels 410 on panels 408. The cassette 400 loaded on the cassette type pedestal 204 has its label 410 held in contact with the head 214 through the opening 414. The recording unit 1212 connects to the identification data control 224 through the lead 218.

Important functions of the identification data control 224 are generating an identification code to be assigned to a panel 408 at each shot and supply it to the identification code recorder 1212, and mating the identification code with input data supplied through the keyboard 220, card reader 222 and lead 226. To accomplish these functions, the control 224 is provided with a register or a memory for the temporary storage of the identification code and input data. The control 224 is also provided with a counter or like circuitry capable of generating a particular identification code every time the shot control device 250 on the pedestal is operated by the technician to deliver a trigger signal ST to the circuitry via the lead 228. For example, the identification code particular to a panel 408 is a string of numerals distinguishable from others and which may include a fixed portion and a variable portion. The fixed portion of the code may designate a terminal unit 202 of the exposure room 200 in which the terminal unit 202 is located. The fixed portion may be semipermanently programmed in the identification data control 224. The variable portion, on the other hand, may be one of various sets of numerals concerned only with a specific terminal unit 202, such as one which indicates the date in its upper bits and one of serial numbers of that date. Available as the trigger signal ST is, for example, a shot signal from a shoot button (not shown) or a panel feed signal in the shot control apparatus 250 associated with a pedestal 204. In response to a trigger signal ST, the identification data control 224 supplies the generated identification code to the identification recorder 1212 so that the head 214 records the codes in the label 410. At the same time, the control 224 feeds the identification code and input data to the transmission control 232 through the lead 230.

To sum up the operation, in the event of exposure of a panel 408 to an image radiation in any one of the rooms 200B-200N, the identification data control 224 generates an identification code particular to the panel 408. The head 1214 then records the identification code in the label 410 adhered to the panel 408. Simultaneously, the control 224 combines for each shot the identification code with the object data, exposure data and imaging data entered through the keyboard 220, card reader 222 and sensor 252. The combined information is delivered to the central control system 300 through the transmission control 232 and transmitter 236. Exposed panels 408 in each exposure room are brought together to the image processing room 100. The central control system 300, under the control of the central control 316, sequentially stores in the file storage 318 all the panel identification codes and object and exposure data coming in through the transmission circuits 404B-404N. The sensor 1322 reads the identification code on the label 410 of a panel 408 before the reading system 102 reads the image stored in the panel 408. The central control 316 is supplied with the identification code and extracts the object and exposure data mating with the specific identification code out of the file storage 318. Based on such information, the central control 316 processes the image stored in the panel 408. The processed image signal is fed through the formator 334 to the laser recording system 338 so that the image and data are visibly reproduced on a film 340.

Figure 7:
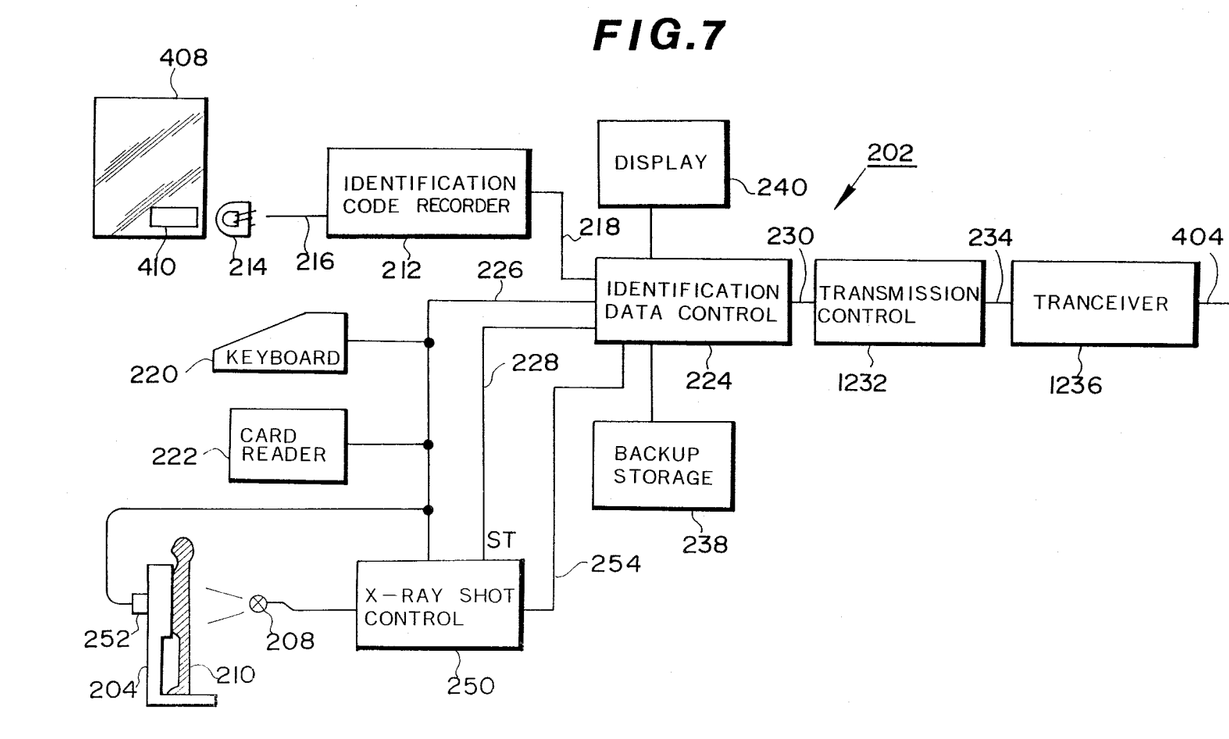
FIGS. 7 and 8 are block diagrams showing still another embodiment of the present invention.
Figure 8:
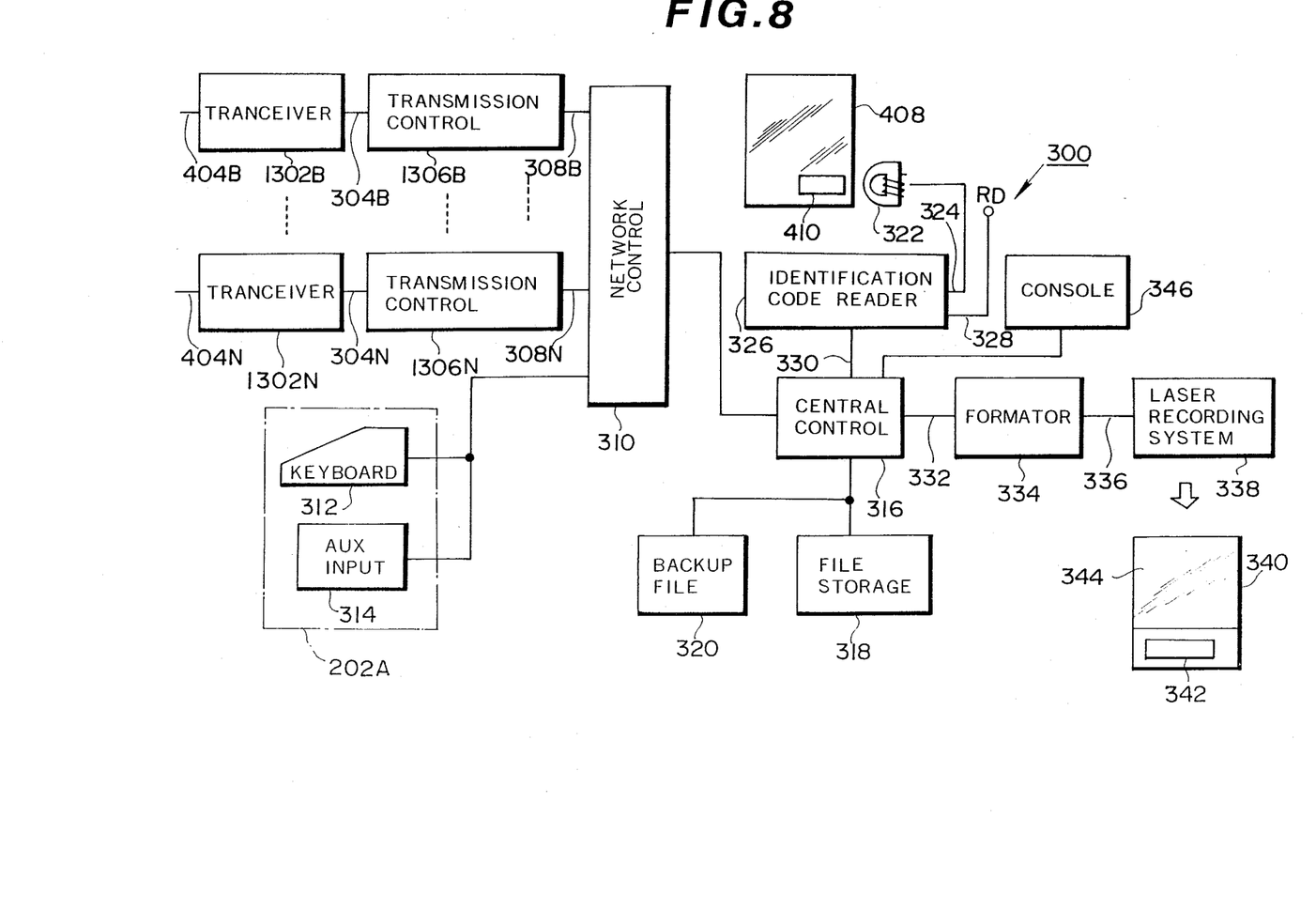

Referring to FIGS. 7 and 8, still another embodiment of the present invention is shown which is essentially similar to the embodiment described above with reference to FIGS. 5 and 6. The difference is that, in FIGS. 7 and 8, identification codes are assigned to individual panels 408 by the central control 316 of the central control system 300. Thus, the system shown in FIGS. 7 and 8 includes a transmission control 1232 and a transceiver 1236 in each terminal unit 202, communication circuits 404B-404N, and transceivers 1302B-1302N and transmission controls 1306B-1306N in the central control system 300, all of which are capable of both transmitting and receiving data signals. This is a contrast to the corresponding transmission control 232 and transmitter 236 in each terminal unit 202, communication circuits 404B-404N, and receivers 302B-302N and reception controls 306B-306N included in the arrangement of FIGS. 5 and 6. It follows that the identification data control 224 of FIG. 7, different from that of FIG. 5, does not require the function of generating identification codes for panels 408.

Figure 9A:
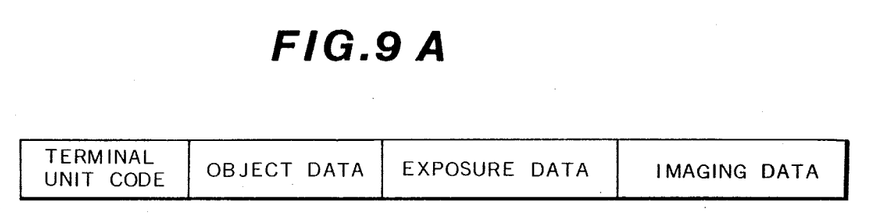
FIGS. 9A and 9B are views of an exemplary format of a message block exchanged between a terminal unit and a central control system shown in FIGS. 7 and 8.

Object data, exposure data, imaging data and others required are entered into an identification data control 224 at a terminal unit 202 through the keyboard 220, card reader 222 and sensor 252. Thereafter, the shoot button (not shown) on the shot control apparatus 250 is operated to expose a panel 408 to an image radiation. In response to the resulting trigger signal ST on the lead 228, the identification data control 224 supplies the central control system 300 the inputted data together with a code identifying the specific terminal unit 202, through the transmission control 1232, transceiver 1236 and transmission circuit 404. An example of the data format is illustrated in FIG. 9(A).

Figure 9B:
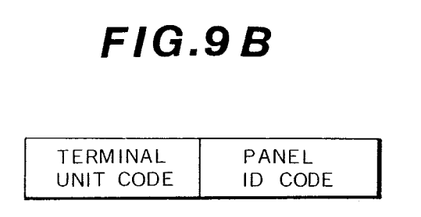

The central control 316 of the central control system 300 shown in FIG. 8 receives the input data coming in through the corresponding transceiver 1302B-1302N, transmission control 1306B-1306N and transmission network control 310. Then, the central control 316 composes an identification code particular to the input data train, that is, particular to an exposure carried out at that time in the exposure room 200B-200N with the terminal unit 202B-202N which sent the data to the central control system 300. The identification code is sent back to the terminal unit 202 through the path common to but opposite in direction to the path of data reception. An exemplary data format to be supplied to the terminal unit is shown in FIG. 9(B). The identification code may, but not necessarily, include an identification code for the terminal unit 202B-202N to facilitate statistical processing of input data. The particular identification codes may be replaced by simple serial numbers sequentially provided by the central control system 300. In any case, the central control 316 has in its memory a table or a counter for assigning identification codes as mentioned.

At the terminal unit 202B-202N, the identification code recorder 212 and recording head 214 record the returned panel identification code in the label 410 on the panel 408, under the control of the identification data control 224.

In accordance with this embodiment, every time a request for an identification code arrives at the central control 316 from a terminal unit 202B-202N, that is, in response to the reception of data, the central control 316 assigns an identification code unconditionally to the panel 408 regardless of the terminal units 202B-202N. This promotes efficient use of the storage areas of the file storage 318. The central control 316 needs only to sequentially allot the storage areas of the file storage 318 to input data from the terminal units 202B-202N and store them in the different storage areas, each time input data from any one of the terminals units is received. Data can afterwards be searched for easily and quickly on the basis of the panel identification codes. While use has been made of a label 410 made of a magnetic recording medium 410, it may be replaced by any other suitable magnetically recordable portion of a panel 408 such as a magnetic recording material simply applied to the panel 408.

In summary, it will be seen that the present invention provides a data processing system for a radiation image reproducing apparatus which is capable of efficiently managing exposed radiation image storage panels and processing them in accordance with exposure conditions of images stored in the panels, with the aid of identification codes assigned to the individual panels. The panel identification codes are entered into the system by means of bar codes or the like which can be read mechanically or labels made of a magnetic recording material adhered to the panels to be magnetically recorded with particular identification codes. This, coupled with the entry of other data through a keyboard and a magnetic card reader, presents a minimum possibility of errors and promotes the ease of handling. The panel identification codes and other data thus entered are filed in a storage and searched for on the basis of the identification codes which are read while the images in the panels are read, so that numerous kinds of multiple panels can be processed concentratively within a short period of time. Because a single central control system can accommodate a plurality of terminal units, it is possible to increase the number of terminal units to meet a desired scale of the system. The system operates with excellent reliability due to the redundancy employed to cope with circuit failures and system downs. Thus, individual panels can be managed in concentration to a significant degree of reliability.

While this invention has been described in terms of a specific illustrative embodiments, it is to be understood to be susceptible of modification by those skilled in the art within the spirit and scope of the appended claims.

What is claimed is:

1. A radiation image processing system comprising:
    a plurality of exposing devices remote from a central image processing station for exposing radiation image storage panels having a stimulable phosphor layer responsive to radiation transmitted through an object to store a radiation image of the object, each of said radiation image storage panels further having label means suitable for associating an identification code with said radiation image storage panel;
    an input means provided in the vicinity of each of said exposing devices for receiving an identification code assigned to a storage panel and data related to a radiation exposure of said radiation image storage panel at the exposing device;
    transmission means for transmitting signals representative of the identification code and the data; and
    a single central image processing station for said plurality of exposing devices which comprises receiving means for receiving and storing the identification code and the data transmitted by said transmission means and to correlate a storage panel with stored data by means of the identification code, and image processing means for processing a radiation image stored in the storage panel in accordance with the correlated data,
    said image processing means comprising a reading device for photoelectrically reading the radiation image stored in the storage panel by exposing the panel to stimulating rays to thereby produce an electrical signal associated threwith, and an image reproducing device for reproducing the radiation image based on both the electrical signal, and on the data correlated to said storage panel by means of the identification code.

2. A data processing system as claimed in claim 1, further comprising recording means for recording in the storage panel an identification code particular to the panel in the event of an exposure at the exposing device.

3. A data processing system as claimed in claim 2, in which the recording means includes means for generating a particular identification code.

4. A data processing system as claimed in claim 2, wherein said input means includes receiver means for receiving a particular identification code assigned at the image reproducing device in relation with an exposure at the exposing device, the recording means recording in the storage panel the identification code received by the receiver means of said input means.

5. A data processing system as claimed in claim 1, in which the input means includes reading means for reading an identification code assigned to the storage panel and data related with the exposure.

6. A data processing system as claimed in claim 1, in which the input means includes a manually operable input device which is manually operable to enter the data related with the exposure into the input means.

7. A data processing system as claimed in claim 1, in which the input means includes sensor means for sensing the conditions of an exposure carried out at the exposing device.

8. A data processing system as claimed in claim 1, further comprising display means connected to said input means for displaying the condition in which the identification code of the storage panel and predetermined data related with the exposure have not previously been entered into the input means upon making an exposure at the exposing device.

9. A data processing system as claimed in claim 1, further comprising means connected to said input means and said exposing device for inhibiting the radiation function of the exposing device at the time of an exposure unless at least the identification code of the storage panel and predetermined data related with the exposure have been previously entered into the input means.

10. A data processing system as claimed in claim 1, wherein said image processing means further comprises:
    storage means for storing data related with an exposure while matching the data with an identification code;
    first reading means provided in the vicinity of the image reading device for reading the identification code provided on the exposed storage panel provided to the image reading device; and
    searching means for searching for data stored in said storage means which matches the identification code read by the first reading means.

11. A data processing system as claimed in claim 10, in which the input means includes a second reading means for reading an identification code assigned to the storage panel and data related with the exposure.

12. A data processing system as claimed in claim 10, in which the input means includes a manually operable input means which is manually operable to enter the data related with the exposure into the input means.

13. A data processing system as claimed in claim 10, in which the input means includes a sensor means for sensing the conditions of an exposure carried out at the exposing device.

14. A data processing system as claimed in claim 10, in which the searching means includes recording means for recording the searched data as a visible image on a recording medium together with the radiation image read by the image reading device.

15. A data processing system as claimed in claim 14, further comprising a backup storage device provided in the vicinity of the exposing device to store in a storage medium thereof the identification code and the corresponding data entered into the input means, and auxiliary means for reading the identification code and its corresponding data out of said storage medium and storing said code and data in the storage means.

16. A data processing system as claimed in claim 14, further comprising second input means for receiving the identification code of a storage panel and data related with the panel, said second input means being provided in the vicinity of the image reading device.

17. A data processing system as claimed in claim 14, in which the first reading means includes means for manually entering the identification code of a storage panel.

18. A data processing system as claimed in claim 1, in which a plurality of the exposing devices are provided, an input means being provided to each of the exposing devices.

19. A radiation image processing system as claimed in claim 1, wherein said image processing means further comprises means to sense the identification code assigned to the storage panel to identify the specific panel, and means to obtain the data correlated to said storage panel by the identification code, from said receiving means.

20. A radiation image processing system as claimed in claim 19, further including means for determining the conditions on photoelectrically reading out the radiation image stored in the storage panel in response to the data correlated to said storage panel.

21. A radiation image processing system as claimed in claim 20, further including means for visually indicating said data correlated to said storage panel and the conditions used in photoelectrically reading out the radiation image together with the reproduced radiation image.

22. A radiation image processing system comprising:
a plurality of exposing devices remote from a central image processing station for exposing a radiation image storage panel having a stimulable phosphor layer responsive to radiation transmitted through an object to store a radiation image of the object said radiation image storage panel further having label means suitable for associating an identification code with said radiation image storage panel;
a plurality of input means at least one input means being provided in the vicinity of each exposing device for receiving an identification code assigned to the storage panel and data related to a radiation exposure of said storage panel at the exposing device;
interlock means connected to said input means and its corresponding exposing device for inhibiting the radiation function of an exposing device, unless at least the identification code of the storage panel and predetermined data related to the exposure have been previously received by said input means;
transmission means for transmitting signals representative of the identification code and the data; and
a central image processing station which comprises receiving means for receiving and storing the identification code and the data transmitted by said transmission means and to correlate a storage panel with stored data by means of the identification code, and image processing means for processing a radiation image stored in the storage panel in accordance with the correlated data.
said image processing comprising a reading device for photoelectrically reading the radiation image stored in the storage panel by exposing the panel to simulating rays to thereby produce an electrical signal associated therewith, and an image reproducing device for reproducing the radiation image based on both the electric signal, and on the data correlated to said storage panel by means of the identification code.

23. A radiation image processing system comprising:
a plurality of exposing devices remote from a central image processing station for exposing a radiation image storage panel having a stimulable phosphor layer responsive to radiation transmitted through an object to store a radiation image of the object said radiation image storage panel further having label means suitable for associating an identification code with said radiation image storage panel;
recorder means provided in the vicinity of said respective exposing devices, said recorder means for receiving a particular identification code assigned to a radiation storage panel by said central image processing station in relation to an exposure at the exposing device, and recording the particular identification code on the label means of said radiation image storage panel;
a plurality of input means, at least one output means being provided in the vicinity of each exposing device for receiving an identification code assigned to the storage panel and data related to a radiation exposure of said storage panel at the exposing device;
transmission means for transmitting signals representative of the identification code and the data; and
a central image processing station which comprises receiving means for receiving and storing the identification code and the data transmitted by said transmission means and to correlate a storage panel with stored data by means of the identification code, and image processing means for processing a radiation image stored in the storage panel in accordance with correlated data,
said image processing means comprising a reading device for photoelectrically reading the radiation image stored in the storage panel by exposing the panel to stimulating rays to thereby produce an electrical signal associated therewith, and an image reproducing device for reproducing the radiation image based on both the electric signal, and on the data correlated to said storage panel by means of the identification code.

24. A radiation image processing system comprising:
a plurality of exposing devices remote from a central image processing station for exposing a radiation image storage panel having a stimulable phosphor layer responsive to radiation transmitted through an object to store a radiation image of the object said radiation image storage panel further having label means suitable for associating an identification code with said radiation image storage panel;
recorder means provided in the vicinity of said respective exposing devices, said recorder means for generating a particular identification code to be assigned to a radiation image storage panel in relation to an exposure at the exposure device, and recording the particular identification code on the label means of said radiation image storage panel;
a plurality of input means, at least one input means being provided in the vicinity of each exposing device for receiving an identification code assigned to the storage panel and data related to a radiation exposure of said storage panel at the exposing device;
transmission means for transmitting signals representative of the identification code and the data; and
a central image processing station which comprises receiving means for receiving and storing the identification code and the data transmitted by said transmission means and to correlate a storage panel with stored data by means of the identification code, and image processing means for processing a radiation image stored in the storage panel in accordance with correlated data,
said image processing means comprising a reading device for photoelectrically reading the radiation image stored in the storage panel by exposing the panel to stimulating rays to thereby produce an electrical signal associated therewith, and an image reproducing device for reproducing the radiation image based on both the electric signal, and on the data correlated to said storage panel by means of the identification code.

25. A radiation image processing system comprising:
a plurality of exposing devices remote from a central image processing station for exposing a radiation image storage panel having a stimulable phosphor layer responsive to radiation transmitted through an object to store a radiation image of the object said radiation image storage panel further having a machine readable label associating a particular identification code with said radiation image storage panel;
a plurality of input means, at least one input means being provided in the vicinity of each exposing device, each input means including first reading means for reading said machine readable label to obtain the particular identification code associated with said radiation image storage panel, and receiving means for receiving data related with a radiation exposure of said radiation image storage panel at the exposing device;
transmission means for transmitting signals representative of the identification code and the data; and
a central image processing station which comprises receiving means for receiving and storing the identification code and the data transmitted by said transmission means and to correlate a storage panel with stored data by means of the identification code, and image processing means for processing a radiation image stored in the storage panel in accordance with correlated data,
said image processing means comprising a second reading means for reading and machine readable label to obtain the particular identification code associated with a radiation image storage panel to be processed, a reading device for photoelectrically reading the radiation image stored in the storage panel by exposing the panel to stimulating rays to thereby produce an electrical signal associated therewith, and an image reproducing device for reproducing the radiation image based on both the electric signal, and on the data correlated to said storage panel by means of the identification code.

26. A radiation image processing system comprising:
a plurality of exposing devices remote from a central image processing station for exposing radiation image storage panels having a stimulable phosphor layer responsive to radiation transmitted through an object to store a radiation image of the object, each of said radiation image storage panels further having label means suitable for associating an identification code with said radiation image storage panel;
a single input means common to at least two of said exposure devices for receiving an identification code assigned to a storage panel and data related to a radiation exposure of said radiation image storage panel at the exposing device;
a single central image processing station for said plurality of exposing devices which comprises receiving means for receiving and storing the identification code and the data transmitted by said transmission means and to correlate a storage panel with stored data by means of the identification code, and image processing means for processing a radiation image storage in the storage panel in accordance with the correlated data,
said image processing means comprising a reading device for photoelectrically reading the radiation image stored in the storage panel by exposing the panel to stimulating rays to thereby produce an electrical signal associated therewith, and an image reproducing device reproducing the radiation image based on both the electric signal, and on the data correlated to said storage panel by means of the identification code.

27. A radiation image processing system as claimed in claim 26, further including additional input means, one for each exposure device which does not share said single common input means each of said additional input means being in the vicinity of a respective exposure device, each of said additional input means for receiving an identification code assigned to a storage panel and data related to a radiation exposure of said radiation image storage panel at the exposing device.

* * * * *